(12) United States Patent
Ishii et al.

(10) Patent No.: US 7,985,880 B2
(45) Date of Patent: Jul. 26, 2011

(54) METHOD FOR PRODUCING OPTICALLY ACTIVE 1-(FLUORO-, TRIFLUOROMETHYL- OR TRIFLUOROMETHOXY-SUBSTITUTED PHENYL) ALKYLAMINE N-MONOALKYL DERIVATIVE

(75) Inventors: Akihiro Ishii, Saitama (JP); Kaori Mogi, Fujimino (JP); Hideyuki Tsuruta, Fujimino (JP); Kenjin Inomiya, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 408 days.

(21) Appl. No.: 12/306,837

(22) PCT Filed: Jun. 25, 2007

(86) PCT No.: PCT/JP2007/062688
§ 371 (c)(1),
(2), (4) Date: Dec. 29, 2008

(87) PCT Pub. No.: WO2008/001719
PCT Pub. Date: Jan. 3, 2008

(65) Prior Publication Data
US 2009/0326272 A1 Dec. 31, 2009

(30) Foreign Application Priority Data
Jun. 30, 2006 (JP) .................................. 2006-182236

(51) Int. Cl.
*C07C 209/00* (2006.01)
(52) U.S. Cl. ........................ 564/385; 364/384; 364/304
(58) Field of Classification Search .................. None
See application file for complete search history.

(56) References Cited

U.S. PATENT DOCUMENTS

| 7,186,865 | B2 | 11/2004 | Ishii et al. |
| 7,368,609 | B2 | 6/2007 | Ishii et al. |
| 2004/0235961 | A1* | 11/2004 | Ishii et al. ............ 514/649 |

FOREIGN PATENT DOCUMENTS

| JP | 2000-256278 | 9/2000 |
| JP | 2002-003453 | 1/2002 |
| JP | 2002-187873 | 7/2002 |
| JP | 2002-308836 | 10/2002 |
| JP | 2004-99480 | 4/2004 |
| JP | 2004-182602 | 7/2004 |
| WO | WO 01/25219 | 4/2001 |
| WO | WO 02/32867 | 4/2002 |
| WO | WO 2004/022521 | 3/2004 |

OTHER PUBLICATIONS

G. H. Posner and C. E. Whitten, "Methyl and n-Alkyl Ketones From Carboxylic Acid Chlorides and Organocopper Reagents," Tetrahedron Letters No. 53, pp. 4647-4650, 1970. Pergamon Press, Great Britain.
John McMurry, "McMurry Yuki Kagaku," $4^{th}$ edition, 1998, pp. 960-964.
Edited by CSJ: The Chemical Society of Japan, "Jikken Kagaku Koza," Yuki gosei II- Alcohol/Amine-, vol. 20., $4^{th}$ edition, 1992, pp. 284, 285, 300-302.
International Search Report and Written Opinion dated Aug. 7, 2007 including English translation of the relevant portion (Ten (10) pages).
Informal Comments submitted by applicant in response to the Written Opinion dated Aug. 7, 2007.

* cited by examiner

*Primary Examiner* — Sudhakar Katakam
(74) *Attorney, Agent, or Firm* — Crowell & Moring LLP

(57) ABSTRACT

There is provided a method for producing an optically active 1-(fluoro-, trifluoromethyl- or trifluoromethoxy-substituted phenyl)alkylamine N-monoalkyl derivative, which includes the steps of conducting reductive alkylation of an optically active secondary amine and a formaldehyde (including an equivalent thereof) or lower aldehyde in the presence of a transition metal catalyst under a hydrogen gas atmosphere, thereby converting the secondary amine to an optically active tertiary amine of the formula, and subjecting the tertiary amine to hydrogenolysis. The target optically active compound can be produced efficiently by this production method.

12 Claims, No Drawings

METHOD FOR PRODUCING OPTICALLY ACTIVE 1-(FLUORO-, TRIFLUOROMETHYL- OR TRIFLUOROMETHOXY-SUBSTITUTED PHENYL) ALKYLAMINE N-MONOALKYL DERIVATIVE

TECHNICAL FIELD

The present invention relates to a method for producing an optically active 1-(fluoro-, trifluoromethyl- or trifluoromethoxy-substituted phenyl)alkylamine N-monoalkyl derivative, which is useful as important intermediates for medicines and agricultural chemicals.

BACKGROUND OF THE INVENTION

Optically active 1-(fluoro-, trifluoromethyl- or trifluoromethoxy-substituted phenyl)alkylamine N-monoalkyl derivatives are useful as important intermediates for medicines and agricultural chemicals. Patent Publication 1 and Patent Publication 2 discloses optically active 1-(3,5-bis-trifluoromethyl phenyl)ethylamine N-monoalkyl derivatives and production methods thereof.

Further, the present applicant discloses an optically active 1-(fluoro-, trifluoromethyl- or trifluoromethoxy-substituted phenyl)alkylamine N-monoalkyl derivative and a production method thereof (Patent Document 3) prior to the present application.

Patent Publication 1: International Publication WO 2001/025219

Patent Publication 2: International Publication WO 2002/032867

Patent Publication 3: International Publication WO 2004/022521

SUMMARY OF THE INVENTION

It is an object of the present invention to provide an industrial production method of an optically active 1-(fluoro-, trifluoromethyl- or trifluoromethoxy-substituted phenyl)alkylamine N-monoalkyl derivative, which is useful as important intermediates for medicines and agricultural chemicals.

The production method of the optically active 1-(3,5-bis-trifluoromethyl phenyl)ethylamine N-monoethyl derivative disclosed in Patent Publication 1 involves optical resolution of a racemic modification with an optically active malic acid. It is thus difficult to say that the production method of Patent Publication 1 is an efficient technique.

The production method disclosed by the present application in Patent Publication 3 adopts a technique for asymmetric synthesis of the optically active 1-(fluoro-, trifluoromethyl- or trifluoromethoxy-substituted phenyl)alkylamine N-monoalkyl derivative to be much more practical than the above optical resolution technique, but still has many problems to be solved from the industrial perspectives.

More specifically, it is necessary to use a stoichiometric amount of relatively expensive hydride reducing agent in an asymmetric reduction step. There remain the other problems to be solved, such as improvement in diastereoselectivity, simplification of post-treatment process, avoidance of boron waste effluent and the like. It is also necessary to use a stoichiometric amount of base in an alkylation step. In the case of using a methyl halide as a suitable alkylating agent for methylation, for example, high safety is required for hardware such as equipment and software such as handling in view of the toxicity of methyl halide. Furthermore, there occurs an overalkylation reaction to generate a very small amount of quaternary ammonium salt as a by-product (as indicated in the scheme 1 where $R^3$ is an alkyl group having a carbon number of 1 to 6 and X is a leaving group). In a subsequent hydrogenolysis step, the quaternary ammonium salt can act as a poison to a transition metal catalyst or get converted to a N-dialkyl derivative that is difficult to separate from the target optically active 1-(fluoro-, trifluoromethyl- or trifluoromethoxy-substituted phenyl)alkylamine N-monoalkyl derivative. It is desired to remove this ammonium salt by intricate purification process such as column chromatography for industrially stable high-purity material production.

[Scheme 1]

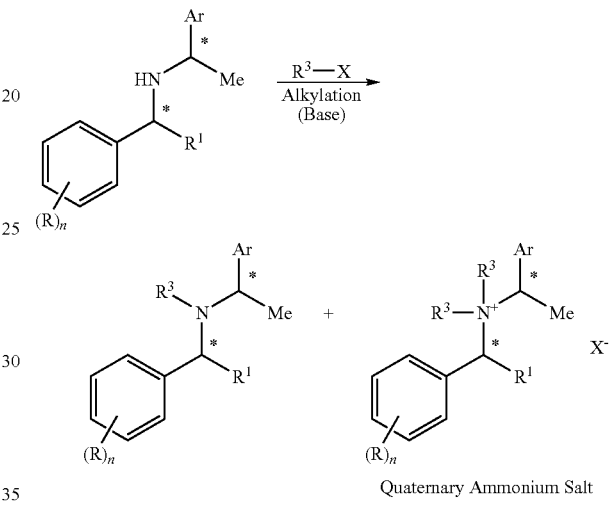

Quaternary Ammonium Salt

The present inventors have conducted extensive researches to solve the above problems and have found that it is possible to produce a target optically active 1-(fluoro-, trifluoromethyl- or trifluoromethoxy-substituted phenyl)alkylamine N-monoalkyl derivative industrially efficiently by the following first process.

Namely, the first process of the present invention is a process for producing an optically active 1-(fluoro-, trifluoro- or trifluoromethoxy-substituted phenyl)alkylamine N-monoalkyl derivative of the formula [4], including: conducting reductive alkylation of an optically active secondary amine of the formula [1] and a formaldehyde (including an equivalent thereof) or lower aldehyde of the formula [2] in the presence of a transition metal catalyst under a hydrogen gas atmosphere, thereby converting the secondary amine to an optically active tertiary amine of the formula [3]; and subjecting the tertiary amine to hydrogenolysis.

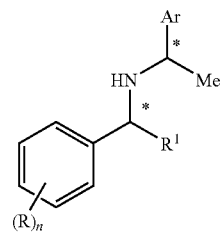

[1]

[2]

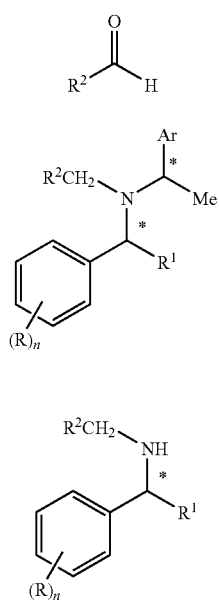

[3]

[4]

In the formulas, R represents a fluorine atom, a trifluoromethyl group or a trifluoromethoxy group; n represents an integer of 1 to 5; the substitution position is arbitrary; $R^1$ represents an alkyl group having a carbon number of 1 to 6; $R^2$ represents a hydrogen atom or an alkyl group having a carbon number of 1 to 5; Me represents a methyl group; Ar represents a phenyl group or a 1- or 2-naphthyl group; and * represents an asymmetric carbon.

The present inventors have further found that it is possible to suitably produce the optically active secondary amine of the formula [1], which is a starting material in the first process, by the following second process.

Namely, the second process of the present invention includes: conducting dehydration condensation of a fluoro-, trifluoromethyl- or trifluoromethoxy-substituted phenyl alkyl ketone of the formula [5] and an optically active primary amine of the formula [6], thereby converting the ketone to an optically active imine of the formula [7]; and subjecting the imine to asymmetric reduction in the presence of a transition metal catalyst under a hydrogen gas atmosphere.

[5]

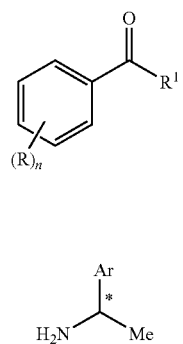

[6]

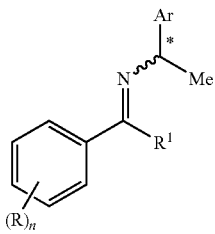

[7]

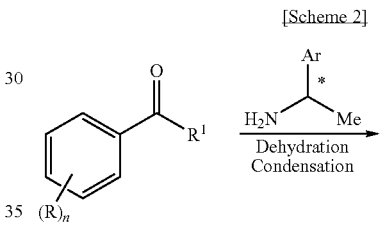

In the formulas, R represents a fluorine atom, a trifluoromethyl group or a trifuluoromethoxy group; n represents an integer of 1 to 5; the substitution position is arbitrary; $R^1$ represents an alkyl group having a carbon number of 1 to 6; Me represents a methyl group; Ar represents a phenyl group or a 1- or 2-naphthyl group; the wavy line represents E configuration or Z configuration; and * represents an asymmetric carbon.

The following scheme indicates a combination of the first and second processes, which contains first to fourth process steps.

[Scheme 2]

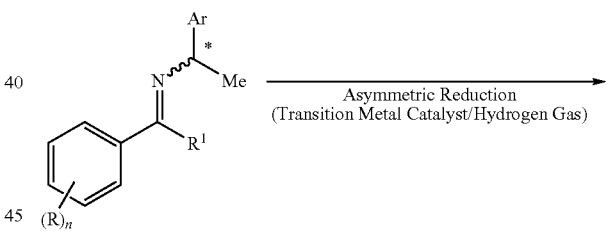

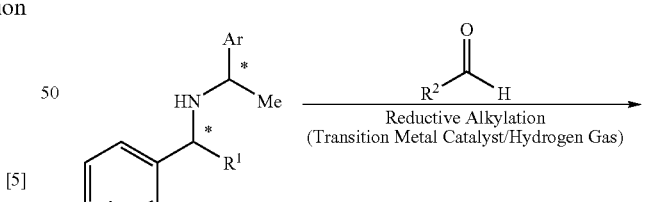

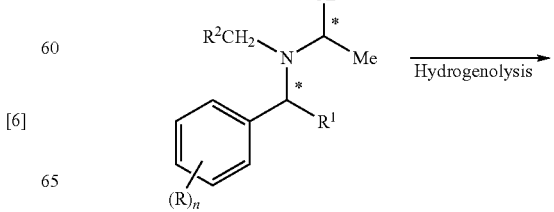

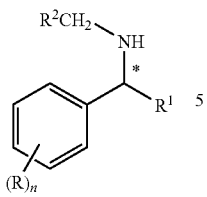

The present invention also provides a third process in which the optically active tertiary amine of the formula [3] is produced by: conducting asymmetric reduction of the optically active imine of the formula [7] in the presence of the transition metal catalyst under the hydrogen gas atmosphere to provide a reaction solution containing the optically active secondary amine of the formula [1]; directly adding the formaldehyde (including its equivalent) or lower aldehyde of the formula [2] to the reaction solution; and conducting reductive alkylation of the secondary amine and the formaldehyde or lower aldehyde under the hydrogen gas atmosphere by the reuse of the transition metal catalyst remaining in the reaction solution.

The present invention further provides a fourth process in which the optically active 1-(fluoro-, trifluoromethyl- or trifluoromethoxy-substituted phenyl)alkylamine N-monoalkyl derivative of the formula [4] is produced with high purity by: converting the N-monoalkyl derivative to an inorganic or organic acid salt; and subjecting the inorganic or organic acid salt to recrystallization purification.

The first process of the present invention may be a process (fifth process) for producing an optically active 1-(trifluoromethyl-substituted phenyl)alkylamine N-monoalkyl derivative of the formula [11], including: conducting reductive alkylation of an optically active secondary amine of the formula [8] and a paraformaldehyde of the formula [9] in the presence of a transition metal catalyst under a hydrogen gas atmosphere, thereby converting the secondary amine to an optically active tertiary amine of the formula [10]; and subjecting the tertiary amine to hydrogenolysis.

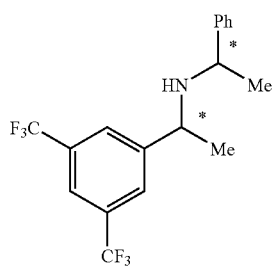

[8]

HO(CH₂O)ₘH  [9]

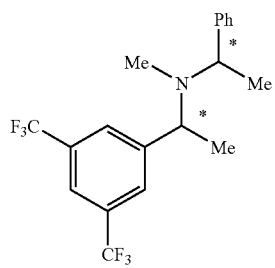

[10]

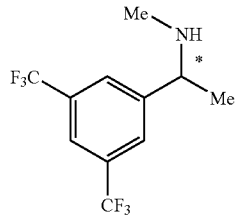

[11]

In the formulas, Me represents a methyl group; Ph represents a phenyl group; m represents a positive integer; and * represents an asymmetric carbon.

The present invention also provides a sixth process for producing the optically active secondary amine of the formula [8], which is a starting material in the fifth process, including: conducting dehydration condensation of a trifluoromethyl substituted phenyl alkyl ketone of the formula [12] and an optically active primary amine of the formula [13], thereby converting the ketone to an optically active imine of the formula [14]; and subjecting the imine to asymmetric reduction in the presence of a transition metal catalyst under a hydrogen gas atmosphere.

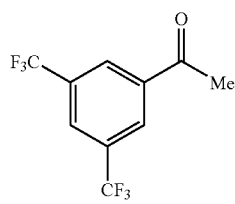

[12]

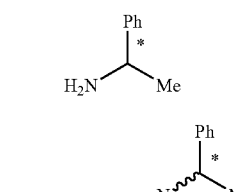

[13]

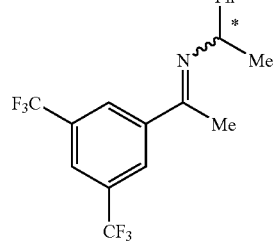

[14]

In the formulas, Me represents a methyl group; Ph represents a phenyl group; the wavy line represents E configuration or Z configuration; and * represents an asymmetric carbon.

The present invention provides a seventh process in which the optically active tertiary amine of the formula [10] is produced by: conducting asymmetric reduction of the optically active imine of the formula [14] in the presence of the transition metal catalyst under the hydrogen gas atmosphere to provide a reaction solution containing the optically active secondary amine of the formula [8]; directly adding the paraformaldehyde of the formula [9] to the reaction solution; and conducting reductive alkylation of the secondary amine and the paraformaldehyde under the hydrogen gas atmosphere by the reuse of the transition metal catalyst remaining in the reaction solution.

Moreover, the present invention provides an eighth process in which the optically active 1-(trifluoromethyl-substituted phenyl)alkylamine N-monoalkyl derivative of the formula [11] is produced with high purity by: converting the N-monoalkyl derivative to an inorganic or organic acid salt; and subjecting the inorganic or organic acid salt to recrystallization purification.

As set forth in the third and seventh processes of the present invention, it has been found that it is possible to produce the optically active tertiary amine by conducting asymmetric reduction to provide the reaction solution of the optically active secondary amine, directly adding the formaldehyde (including its equivalent) or lower aldehyde to the reaction solution and conducting reductive alkylation of the secondary amine and the formaldehyde (including its equivalent) or lower aldehyde under the hydrogen gas atmosphere by the reuse of the transition metal catalyst remaining in the reaction solution. This enables a significant reduction in the total amount of the transition metal catalyst used in the second and third process steps of the scheme 2.

It has been further found, as set forth in the fourth and eighth processes of the present invention, that it is possible to produce the optically active 1-(fluoro-, trifluoromethyl- or trifluoromethoxy-substituted phenyl)alkylamine N-monoalkyl derivative with high purity by, after obtaining the N-monoalkyl derivative by the hydrogenolysis reaction, converting the N-monoalkyl derivative to the inorganic or organic acid salt and subjecting the inorganic or organic acid salt to recrystallization purification.

In the present invention, the asymmetric reduction does not use a hydride reducing agent such as sodium borohydride (and thereby allows avoidance of boron waste effluent) and enables higher diastereoselectivity and much simpler and easier post-treatment process than in the case of using the hydride reducing agent.

Also, the reductive alkylation does not use a base and an alkylating agent e.g. methyl halide, does not give a by-product of quaternary ammonium salt as a result of overalkylation reaction and thus does not require intricate purification process in the present invention.

From the industrial perspectives, the asymmetric reduction and the reductive alkylation can be conducted in one-pot reaction process for high productivity. Further, the high-purity product can be obtained efficiently for use as important intermediates for medicines and agricultural chemicals by recrystallization purification of the inorganic or organic acid salt of the final target compound.

DETAILED DESCRIPTION

Hereinafter, the production method of the optically active 1-(fluoro-, trifluoromethyl- or trifluoromethoxy-substituted phenyl)alkylamine N-monoalkyl derivative according to the present invention will be described below in detail.

The production method of the present invention includes "third process step" and "fourth process step" as two essential steps and optionally includes "first process step" and "second process step", with the proviso that: the first process step is a step for forming the optically active imine of the formula [7] by dehydration condensation of the fluro-, trifluoromethyl- or trifluoromethoxy-substituted phenyl alkyl ketone of the formula [5] and the optically active primary amine of the formula [6]; the second process step is a step for forming the optically active secondary amine of the formula [1] by asymmetric reduction of the optically active imine of the formula [7] in the presence of the transition metal catalyst under the hydrogen gas atmosphere; the third process step is a step for forming the optically active tertiary amine of the formula [3] by reductive alkylation of the optically active secondary amine of the formula [1] and the formaldehyde (including its equivalent) or lower aldehyde of the formula [2] in the presence of the transition metal catalyst under the hydrogen gas atmosphere; and the fourth process step is a step for forming the optically active 1-(fluoro-, trifluoromethyl- or trifluoromethoxy-substituted phenyl)alkylamine N-monoalkyl derivative of the formula [4] by hydrogenolysis of the optically active tertiary amine of the formula [3]. In this case, the production method includes four process steps in total as indicated in the scheme [2].

The first process step: "dehydration condensation" will be first explained below. The first process step is carried out by reacting the fluoro-, trifluoromethyl- or trifluoromethoxy-substituted phenyl alkyl ketone of the formula [5] with the optically active primary amine of the formula [6] in the presence of an acid catalyst.

In terms of stereochemistry, the asymmetric carbon of the optically active imine of the formula [7] has R or S configuration so as to preserve the configuration of the asymmetric carbon of the optically active primary amine reactant material of the formula [6]. (The R or S configured target compound is obtained from the corresponding R or S configured reactant material.)

Examples of $(R)_n$ of the fluoro-, trifluoromethyl- or trifluoromethoxy-substituted phenyl alkyl ketone of the formula [5] are 2-fluoro, 3-fluoro, 4-fluoro, 2,3-difluoro, 2,4-difluoro, 2,5-difluoro, 2,6-difluoro, 3,4-difluoro, 3,5-difluoro, 2,3,4-trifluoro, 3,4,5-trifluoro, 2,4,5-trifluoro, 2,3,5-trifluoro, 2,3,6-trifluoro, 2,4,6-trifluoro, 2,3,5,6-tetrafluoro, 2,4,5,6-tetrafluoro, 3,4,5,6-tetrafluoro, 2,3,4,5,6-pentafluoro, 2-trifluoromethyl, 3-trifluoromethyl, 4-trifluoromethyl, 2,3-bis-trifluoromethyl, 2,4-bis-trifluoromethyl, 2,5-bis-trifluoromethyl, 2,6-bis-trifluoromethyl, 3,4-bis-trifluoromethyl, 3,5-bis-trifluoromethyl, 2,3,4-tris-trifluoromethyl, 3,4,5-tris-trifluoromethyl, 2,4,5-tris-trifluoromethyl, 2,3,5-tris-trifluoromethyl, 2,3,6-tris-trifluoromethyl, 2,4,6-tris-trifluoromethyl, 2,3,5,6-tetrakis-trifluoromethyl, 2,4,5,6-tetrakis-trifluoromethyl, 3,4,5,6-tetrakis-trifluoromethyl, 2,3,4,5,6-pentakis-trifluoromethyl, 2-trifluoromethoxy, 3-trifluoromethoxy, 4-trifluoromethoxy, 2,3-bis-trifluoromethoxy, 2,4-bis-trifluoromethoxy, 2,5-bis-trifluoromethoxy, 2,6-bis-trifluoromethoxy, 3,4-bis-trifluoromethoxy, 3,5-bis-trifluoromethoxy, 2,3,4-tris-trifluoromethoxy, 3,4,5-tris-trifluoromethoxy, 2,4,5-tris-trifluoromethoxy, 2,3,5-tris-trifluoromethoxy, 2,3,6-tris-trifluoromethoxy, 2,4,6-tris-trifluoromethoxy, 2,3,5,6-tetrakis-trifluoromethoxy, 2,4,5,6-tetrakis-trifluoromethoxy, 3,4,5,6-tetrakis-trifluoromethoxy and 2,3,4,5,6-pentakis-trifluromethoxy. Among others, mono-substituents $[(R)_1]$ where n is 1 and bis-substituents $[(R)_2]$ where n is 2 are preferred. More preferred are 3,5-bis-substitutents where R is trifluoromethyl and n is 2 (i.e. 3,5-bis-trifluoromethyl group).

Examples of $R^1$ of the fluoro-, trifluoromethyl- or trifluoromethoxy-substituted phenyl alkyl ketone of the formula [5] are methyl, ethyl, 1-propyl, 2-propyl, cyclopropyl, 1-butyl, 2-butyl, 2-methyl-1-propyl, t-butyl, cyclobutyl, 1-pentyl, 2-pentyl, 3-pentyl, neopentyl, t-amyl, cyclopentyl, 1-hexyl, 2-hexyl, 3-hexyl and cyclohexyl. Among others, an alkyl group having a carbon number of 4 or smaller is preferred. Methyl i.e. an alkyl group having a carbon atom of 1 is more preferred.

Depending on the combination of $(R)_n$ and $R^1$, the fluoro-, trifluoromethyl- or trifluoromethoxy-substituted phenyl alkyl ketone of the formula [5] can be a novel compound and can be produced in the same manner as disclosed in "Tetrahedron Letters", No. 53, pp. 4647-4650, 1970 etc.

Examples of Ar of the optically active primary amine of the formula [6] are phenyl, 1-naphthyl and 2-naphthyl. Among others, phenyl and 2-naphthyl are preferred. More preferred is phenyl.

In terms of stereochemistry, the asymmetric carbon of the optically active primary amine of the formula [6] has R or S configuration. The configuration of the optically active primary amine of the formula [6] can be selected appropriately depending on the absolute configuration of the final target compound.

There is no particular restriction on the enantiomeric excess (ee) of the optically active primary amine of the formula [6]. It suffices that the optically active primary amine of the formula [6] has an enantiomeric excess of 95% ee or higher. The enantiomeric excess of the optically active primary amine of the formula [6] is generally preferably 97% ee or higher, more preferably 99% ee or higher.

There is no particular restriction on the amount of the optically active primary amine of the formula [6] used. It suffices to use 1 mol or more of the optically active primary amine of the formula [6] per 1 mol of the fluoro-, trifluoromethyl- or trifluoromethoxy-substituted phenyl alkyl ketone of the formula [5]. The optically active primary amine of the formula [6] is generally preferably used in the amount of 1 to 5 mol, more preferably 1 to 3 mol, per 1 mol of the fluoro-, trifluoromethyl- or trifluoromethoxy-substituted phenyl alkyl ketone of the formula [5].

Examples of the acid catalyst are inorganic acids such as hydrochloric acid, sulfuric acid, phosphoric acid, zinc chloride, titanium tetrachloride and tetraisopropoxytitanium and organic acids such as benzenesulfonic acid, p-toluenesulfonic acid and 10-camphorsulfonic acid. Among others, sulfuric acid, zinc chloride and p-toluenesulfonic acid are preferred. More preferred are zinc chloride and p-toluenesulfonic acid.

There is no particular restriction on the amount of the acid catalyst used. It suffices that the acid catalyst is used in a catalytic amount per 1 mol of the fluoro-, trifluoromethyl- or trifluoromethoxy-substituted phenyl alkyl ketone of the formula [5]. The acid catalyst is generally preferably used in the amount of 0.001 to 0.9 mol, more preferably 0.005 to 0.5 mol, per 1 mol of the fluoro-, trifluoromethyl- or trifluoromethoxy-substituted phenyl alkyl ketone of the formula [5].

As the present process step involves a dehydration reaction between the fluoro-, trifluoromethyl- or trifluoromethoxy-substituted phenyl alkyl ketone of the formula [5] and the optically active primary amine of the formula [6], it is desirable to carry out the reaction while removing by-product water. It is particularly desirable to carry out the reaction under reflux condition by using a reaction solvent, which is nonmiscible with water, lower in specific gravity than water and azeotropic with water, and removing by-product water with a Dean-Stark trap.

Preferred examples of the reaction solvent are aromatic hydrocarbon solvents such as benzene, toluene, ethyl benzene, xylene and mesitylene. Toluene is more preferred. These reaction solvents can be used solely or in combination thereof.

There is no particular restriction on the amount of the reaction solvent used. The reaction solvent is preferably used in the amount that can theoretically remove by-product water by azeotropic distillation. It is more preferable to reduce the amount of the reaction solvent by means of the Dean-Stark trap. Alternatively, the reaction can be carried out in neat form without using the reaction solvent.

There is no particular restriction on the temperature condition. It is preferable to carry out the reaction at around a temperature from the azeotropic point of the reaction solvent and water to the boiling point of the reaction solvent, more preferably at around the boiling point of the reaction solvent used.

There is no particular restriction on the reaction time. It is preferable to carry out the reaction within 48 hours. As the reaction time varies depending on the reaction substrate and the reaction conditions, it is more preferable to monitor the progress of the reaction by analytical means such as gas chromatography, thin-layer chromatography, liquid chromatography or nuclear magnetic resonance spectroscopy and finish the reaction at the time almost all of the reactant materials disappear.

The target optically active imine of the formula [7] can be obtained by performing ordinary post-treatment on the reaction solution. That is, the excess of the optically active primary amine of the formula [6] can be removed selectively by washing an organic phase containing the optically active imine of the formula [7] in toluene, methylene chloride, ethyl acetate or the like with an aqueous acid solution such as ammonium chloride, acetic acid or hydrochloric acid solution. The high-purity reaction product can be obtained by subjecting the crude product to purification process such as activated carbon treatment, distillation, washing with organic solvent e.g. toluene, ethyl acetate or methanol, and recrystallization as required.

The carbon-nitrogen double bond of the optically active imine of the formula [7] has E or Z configuration in terms of stereochemistry. The ratio of the E and Z configurations of the optically active imine of the formula [7] varies depending on the reaction substrate and the reaction conditions.

Next, the second process step: "asymmetric reduction" will be explained below. The second process step is carried out by reacting the optically active imine of the formula [7] with hydrogen gas in the presence of the transition metal catalyst.

In terms of stereochemistry, the newly-generated asymmetric carbon of the optically active secondary amine of the formula [1] has R or S configuration. Accordingly, there exists R-R configuration, S-R configuration, R-S configuration or S-S configuration (where the character before the hyphen identifies the absolute configuration of the asymmetric carbon of the 1-(fluoro-, trifluoromethyl- or trifluoromethoxy-substituted phenyl)alkyl group and the character after the hyphen identifies the absolute configuration of the asymmetric carbon of the α-arylethyl chiral auxiliary group) as the combination of the configurations of the two asymmetric carbons of the optically active secondary amine of the formula [1]. The degree of asymmetric induction (the diastereomeric excess (de)) of the optically active secondary amine varies depending on the reaction substrate, the transition metal catalyst and the reaction conditions. In the present invention, the major diastereomer of the optically active secondary amine is R-R or S-S configured. The R or S configured final target compound is thus suitably produced using these diastereomers. (The R configured final target compound is obtained from the R-R or R-S configured reactant material, whereas the S configured final target compound is obtained from the S-R or S-S configured reactant material.)

Examples of the transition metal catalyst are platinum catalysts such as platinum black, platinum/activated carbon, platinum/graphite, platinum/alumina, platinum/zirconia and platinum oxide, nickel catalysts such as reduced nickel, Raney nickel, Raney nickel sponge and platinum-doped Raney nickel, iridium catalysts such as iridium black, iridium/calcium carbonate and iridium oxide and palladium catalysts such as palladium black, palladium sponge, palladium/activated carbon, palladium/alumina, palladium/calcium carbonate, palladium/strontium carbonate, palladium/barium sulfate, palladium hydroxide, palladium acetate and palladium chloride. Among others, platinum catalysts and nickel catalysts are preferred. More preferred are platinum/activated carbon, platinum/graphite, platinum/alumina, platinum oxide and Raney nickel sponge. These transition metal catalysts can be used solely or in combination thereof. In the case of the transition metal catalyst having a transition metal on a catalyst support, there is no particular restriction on the amount of the transition metal on the catalyst support. It suffices that the amount of the transition metal on the catalyst support is 0.1 to 50 wt %. The amount of the transition metal on the catalyst support is generally preferably in the range of 0.5 to 30 wt %, more preferably 1 to 20 wt %. The transition metal catalyst may be of hydrous form. Further, the transition metal catalyst may be stored in an inert liquid or water in order to attain higher handling safety or avoid metal surface oxidation.

There is no particular restriction on the amount of the transition metal catalyst used. It suffices that the transition metal catalyst is used in a catalytic amount per 1 mol of the optically active secondary amine of the formula [1]. The transition metal catalyst is generally preferably used in the amount of 0.00001 to 0.5 mol, more preferably 0.0001 to 0.3 mol, per 1 mol of the optically active imine of the formula [7].

There is no particular restriction on the amount of the hydrogen gas used. It suffices to use 1 mol or more of the hydrogen gas per 1 mol of the optically active imine of the formula [7]. The hydrogen gas is generally preferably used in an excessive amount under pressurized condition.

There is no particular restriction on the pressurized condition of the hydrogen gas. It suffices to carry out the reaction at 15 MPa or lower of the hydrogen gas pressure. The hydrogen gas pressure is generally preferably in the range from barometric pressure to 10 MPa, more preferably 0.1 to 7 MPa.

Examples of the reaction solvent are aromatic hydrocarbon solvents such as benzene, toluene, ethyl benzene, xylene and mesitylene, halogenated hydrocarbon solvents such as methylene chloride, chloroform and 1,2-dichloroethane, ether solvents such as diethyl ether, tetrahydrofuran, t-butyl methyl ether and 1,4-dioxane and alcohol solvents such as methanol, ethanol, 2,2,2-trifluoroethanol, n-propanol and i-propanol. Among others, toluene, methylene chloride, 1,2-dichloroethane, tetrahydrofuran, t-butyl methyl ether, 1,4-dioxane, methanol, ethanol, 2,2,2-trifluoroethanol and i-propanol are preferred. More preferred are methylene chloride, 1,2-dichloroethane, methanol, ethanol, 2,2,2-trifluoroethanol and i-propanol. These reaction solvents can be used solely or in combination thereof. Alternatively, the reaction can be carried out in neat form without using the reaction solvent.

There is no particular restriction on the amount of the reaction solvent used. It suffices to use 0.01 L (liter) or more of the reaction solvent per 1 mol of the optically active imine of the formula [7]. The reaction solvent is generally preferably used in the amount of 0.03 to 20 L, more preferably 0.05 to 10 L, per 1 mol of the optically active imine of the formula [7].

There is no particular restriction on the temperature condition. It suffices to carry out the reaction in a temperature range of −60 to +200° C. The reaction temperature is generally preferably in the range of −40 to +175° C., more preferably −20 to +150° C.

There is no particular restriction on the reaction time. It is preferable to carry out the reaction within 72 hours. As the reaction time varies depending on the reaction substrate and the reaction conditions, it is more preferable to monitor the progress of the reaction by analytical means such as gas chromatography, thin-layer chromatography, liquid chromatography or nuclear magnetic resonance spectroscopy and finish the reaction at the time almost all of the reactant material disappears.

The target optically active secondary amine of the formula [1] can be obtained with high diastereoselectivity through very simple and easy post-treatment of filtering out the transition metal catalyst from the reaction solution followed by condensing the filtrate. The filtered recovered transition metal catalyst is reusable in the present asymmetric reduction step or in the subsequent reductive alkylation step. In the case of conducting the asymmetric reduction step and the reductive alkylation step in one-pot reaction process, the transition metal catalyst used in the asymmetric reduction step can be directly reused in the reductive alkylation step without filtering and recovering the transition metal catalyst after the asymmetric reduction step. In this case, the post-treatment of the asymmetric reduction step may be omitted to obtain the optically active tertiary amine of the formula [3] by adding the formaldehyde (including its equivalent) or lower aldehyde of the formula [2] to the reaction solution after completion of the asymmetric reduction and then reacting the optically active secondary amine with the formaldehyde (including its equivalent) or lower aldehyde and hydrogen gas.

The third process step: "reductive alkylation" will be explained below. The third process step is carried out by reacting the optically active secondary amine of the formula [1] with the formaldehyde (including its equivalent) or lower aldehyde of the formula [2] and hydrogen gas in the presence of the transition metal catalyst.

As the combination of the configurations of the two asymmetric carbons in the optically active tertiary amine of the formula [3], there exists R-R configuration, S-R configuration, R-S configuration or S-S configuration so as to preserve the combination of the configurations of the two asymmetric carbons of the optically active secondary amine reactant material of the formula [1] as the starting material. (R-R, S-R, R-S or S-S configured target compound is obtained from the R-R, S-R, R-S or S-S configured reactant material.)

Examples of $R^2$ of the formaldehyde (including its equivalent) and lower aldehyde of the formula [2] are a hydrogen atom, methyl, ethyl, 1-propyl, 2-propyl, cyclopropyl, 1-butyl, 2-butyl, 2-methyl-1-propyl, t-butyl, cyclobutyl, 1-pentyl, 2-pentyl, 3-pentyl, neopentyl, t-amyl and cyclopentyl.

There is no particular restriction on the amount of the formaldehyde (including its equivalent) or lower aldehyde used. It suffices to use 1 mol or more of the formaldehyde (including its equivalent) or lower aldehyde per 1 mol of the optically active secondary amine of the formula [1]. The formaldehyde (including its equivalent) or lower aldehyde is generally preferably used in the amount of 1 to 20 mol, more preferably 1 to 10 mol, per 1 mol of the optically active secondary amine of the formula [1].

Examples of the transition metal catalyst are platinum catalysts such as platinum black, platinum/activated carbon, platinum/graphite, platinum/alumina, platinum/zirconia and platinum oxide, nickel catalysts such as reduced nickel, Raney nickel, Raney nickel sponge and platinum-doped Raney nickel, iridium catalysts such as iridium black, iridium/calcium carbonate and iridium oxide and palladium catalysts such as palladium black, palladium sponge, palladium/activated carbon, palladium/alumina, palladium/calcium carbonate, palladium/strontium carbonate, palladium/barium sulfate, palladium hydroxide, palladium acetate and palladium chloride. Among others, platinum catalysts and nickel catalysts are preferred. More preferred are platinum/ activated carbon, platinum/graphite, platinum/alumina, platinum oxide and Raney nickel sponge. These transition metal catalysts can be used solely or in combination thereof. In the case of the transition metal catalyst having a transition metal on a catalyst support, there is no particular restriction on the amount of the transition metal on the catalyst support. It suffices that the amount of the transition metal on the catalyst support is 0.1 to 50 wt %. The amount of the transition metal on the catalyst support is generally preferably in the range of 0.5 to 30 wt %, more preferably 1 to 20 wt %. The transition metal catalyst may be of hydrous form. Further, the transition metal catalyst may be stored in an inert liquid or water in order to attain higher handling safety or avoid metal surface oxidation.

In the case of conducting the asymmetric reduction and the reductive alkylation in one-pot reaction process, the transition metal catalyst used in the asymmetric reduction can be directly reused in the reductive alkylation without filtering and recovering the transition metal catalyst after the asymmetric reduction. The reductive alkylation may be carried out by newly adding the transition metal catalyst of the same kind as or different kind from that used in the asymmetric reduction. (As will be discussed in Examples, the reaction can be carried out without newly adding the transition metal catalyst.)

There is no particular restriction on the amount of the transition metal catalyst used. It suffices that the transition metal catalyst is used in a catalytic amount per 1 mol of the optically active secondary amine of the formula [1]. The transition metal catalyst is generally preferably used in the amount of 0.00001 to 0.5 mol, more preferably 0.0001 to 0.3 mol, per 1 mol of the optically active secondary amine of the formula [1].

There is no particular restriction on the amount of the hydrogen gas used. It suffices to use 1 mol or more of the hydrogen gas per 1 mol of the optically active secondary imine of the formula [1]. The hydrogen gas is generally preferably used in an excessive amount under pressurized condition.

There is no particular restriction on the pressurized condition of the hydrogen gas. It suffices to carry out the reaction at 15 MPa or lower of the hydrogen gas pressure. The hydrogen gas pressure is generally preferably in the range from barometric pressure to 10 MPa, more preferably 0.1 to 7 MPa.

In the present process step, the reaction may be carried out smoothly by the addition of an inorganic or organic acid as an additive. (When the appropriate reaction conditions are adopted, the inorganic or organic acid is not necessarily added.)

Examples of the additive are inorganic acids such as hydrochloric acid, sulfuric acid, nitric acid, hydrobromic acid and hydriodic acid and organic acids such as acetic acid, propionic acid, butyric acid, p-toluenesulfonic acid and 10-camphorsulfonic acid. Among others, hydrochloric acid, sulfuric acid, hydrobromic acid, acetic acid, propionic acid and p-toluenesulfonic acid are preferred. More preferred are hydrochloric acid, sulfuric acid, acetic acid and p-toluenesulfonic acid.

There is no particular restriction on the amount of the additive used. It suffices to use 0.1 mol or more of the additive per 1 mol of the optically active secondary amine of the formula [1]. The additive is generally preferably used in the amount of 0.1 to 100 mol, more preferably 0.1 to 50 mol, per 1 mol of the optically active secondary amine of the formula [1].

Examples of the reaction solvent are aromatic hydrocarbon solvents such as benzene, toluene, ethyl benzene, xylene and mesitylene, halogenated hydrocarbon solvents such as methylene chloride, chloroform and 1,2-dichloroethane, ether solvents such as diethyl ether, tetrahydrofuran, t-butyl methyl ether and 1,4-dioxane and alcohol solvents such as methanol, ethanol, 2,2,2-trifluoroethanol, n-propanol and i-propanol. Among others, toluene, methylene chloride, 1,2-dichloroethane, tetrahydrofuran, t-butyl methyl ether, 1,4-dioxane, methanol, ethanol, 2,2,2-trifluoroethanol and i-propanol are preferred. More preferred are methylene chloride, 1,2-dichloroethane, methanol, ethanol, 2,2,2-trifluoroethanol and i-propanol. These reaction solvents can be used solely or in combination thereof. Alternatively, the reaction can be carried out in neat form without using the reaction solvent.

There is no particular restriction on the amount of the reaction solvent used. It suffices to use 0.01 L or more of the reaction solvent per 1 mol of the optically active secondary amine of the formula [1]. The reaction solvent is generally preferably used in the amount of 0.03 to 20 L, more preferably 0.05 to 10 L, per 1 mol of the optically active secondary amine of the formula [1].

There is no particular restriction on the temperature condition. It suffices to carry out the reaction in a temperature range of −60 to +200° C. The reaction temperature is generally preferably in the range of −40 to +175° C., more preferably −20 to +150° C.

There is no particular restriction on the reaction time. It is preferable to carry out the reaction within 72 hours. As the reaction time varies depending on the reaction substrate and the reaction conditions, it is more preferable to monitor the progress of the reaction by analytical means such as gas chromatography, thin-layer chromatography, liquid chromatography or nuclear magnetic resonance spectroscopy and finish the reaction at the time almost all of the reactant materials disappear.

The target optically active tertiary amine of the formula [3] can be obtained with high chemical purity through very simple and easy post-treatment of filtering out the transition metal catalyst from the reaction solution, condensing the filtrate, diluting the condensed filtrate with an organic solvent e.g. toluene, methylene chloride or ethyl acetate, washing the diluted solution with water followed by condensing the recovered organic phase. In the present invention, the reductive alkylation does not give a quaternary ammonium salt as a by-product as a result of overalkylation reaction and thus does not require intricate purification process. The crude product can be directly subjected to the subsequent hydrogenolysis step. The high-purity reaction product can be obtained by subjecting the crude product to purification process such as activated carbon treatment, distillation, washing with organic solvent e.g. toluene, ethyl acetate or methanol, and recrystallization as required. Further, the filtered recovered transition metal catalyst is reusable in the present reductive alkylation step or in the preceding asymmetric reduction step.

Finally, the fourth process step: "hydrogenolysis" will be explained below. The fourth process step is carried out by reacting the optically active tertiary amine of the formula [3] with hydrogen gas in the presence of a palladium catalyst.

As the hydrogenolysis is also carried out in the presence of the transition metal catalyst (palladium catalyst) under the hydrogen gas atmosphere, the combination of the reductive alkylation and the hydrogenolysis, or the asymmetric reduction, the reductive alkylation and the hydrogenolysis, is possible for one-pot reaction process. In the case where the hydrogenolysis is combined into one-pot reaction process, however, there occurs a considerable amount of N-dialkyl derivative as a by-product, which is difficult to separate from the final target optically active 1-(fluoro-, trifluoromethyl- or trifluoromethoxy-substituted phenyl)alkylamine N-monoalkyl derivative of the formula [4], due to the presence of the formaldehyde (including its equivalent) or lower aldehyde remaining in the reaction solution after the reductive alkylation. Thus, the combination of the asymmetric reduction and the reductive alkylation is most suitable for one-pot reaction process.

In terms of stereochemistry, the asymmetric carbon of the optically active 1-(fluoro-, trifluoromethyl- or trifluoromethoxy-substituted phenyl)alkylamine N-monoalkyl derivative of the formula [4] has R or S configuration so as to preserve the configuration of the asymmetric carbon of the optically active tertiary amine reactant material of the formula [3]. (The R configured target compound is obtained from the R-R or R-S configured reactant material, whereas the S configured target compound is obtained from the S-R or S-S configured reactant material.)

Preferred examples of the palladium catalyst are palladium black, palladium sponge, palladium/activated carbon, palladium/alumina, palladium/calcium carbonate, palladium/strontium carbonate, palladium/barium sulfate, palladium hydroxide, palladium acetate and palladium chloride. Among others, palladium/activated carbon, palladium/alumina, palladium/calcium carbonate and palladium hydroxide are preferred. Palladium/activated carbon and palladium hydroxide are more preferred. These palladium catalysts can be used solely or in combination thereof. In the case of the palladium catalyst having palladium on a catalyst support, there is no particular restriction on the amount of palladium on the catalyst support. It suffices that the amount of palladium on the catalyst support is 0.1 to 50 wt %. The amount of the palladium on the catalyst support is generally preferably in a range of 0.5 to 30 wt %, more preferably 1 to 20 wt %. The palladium catalyst may be of hydrous form. Further, the palladium catalyst may be stored in an inert liquid or water in order to attain higher handling safety or avoid metal surface oxidation.

There is no particular restriction on the amount of the palladium catalyst used. It suffices that the palladium catalyst is used in a catalytic amount per 1 mol of the optically active tertiary amine of the formula [3]. The palladium catalyst is generally preferably used in the amount of 0.00001 to 0.1 mol, more preferably 0.0001 to 0.01 mol, per 1 mol of the optically active tertiary amine of the formula [3].

There is no particular restriction on the amount of hydrogen gas used. It suffices to use 1 mol or more of the hydrogen gas per 1 mol of the optically active tertiary amine of the formula [3]. The hydrogen gas is generally preferably used in an excessive amount under pressurized condition.

There is no particular restriction on the pressurized condition of the hydrogen gas. It suffices to carry out the reaction at 2 MPa or lower of the hydrogen gas pressure. The hydrogen gas pressure is generally preferably in the range from barometric pressure to 1.5 MPa, more preferably 0.05 to 1 MPa.

In the present process step, the reaction may be carried out smoothly by the addition of an inorganic or organic acid as an additive. (When the appropriate reaction conditions are adopted, the inorganic or organic acid is not necessarily added.)

Examples of the additive are inorganic acids such as hydrochloric acid, sulfuric acid, nitric acid, hydrobromic acid and hydriodic acid and organic acids such as acetic acid, propionic acid, butyric acid, p-toluenesulfonic acid and 10-camphorsulfonic acid. Among others, hydrochloric acid, sulfuric acid, hydrobromic acid, acetic acid, propionic acid and p-toluenesulfonic acid. More preferred are hydrochloric acid, sulfuric acid, acetic acid and p-toluenesulfonic acid.

There is no particular restriction on the amount of the additive used. It suffices to use 0.1 mol or more of the additive per 1 mol of the optically active tertiary amine of the formula [3]. The additive is generally preferably used in the amount of 0.1 to 100 mol, more preferably 0.1 to 50 mol, per 1 mol of the optically active tertiary amine of the formula [3].

Examples of the reaction solvent are aromatic hydrocarbon solvents such as benzene, toluene, ethyl benzene, xylene and mesitylene, halogenated hydrocarbon solvents such as methylene chloride, chloroform and 1,2-dichloroethane, ether solvents such as diethyl ether, tetrahydrofuran, t-butyl methyl ether and 1,4-dioxane and alcohol solvents such as methanol, ethanol, 2,2,2-trifluoroethanol, n-propanol and i-propanol. Among others, toluene, methylene chloride, 1,2-dichloroethane, tetrahydrofuran, t-butyl methyl ether, 1,4-dioxane, methanol, ethanol, 2,2,2-trifluoroethanol and i-propanol are preferred. Particularly preferred are methylene chloride, 1,2-dichloroethane, methanol, ethanol, 2,2,2-trifluoroethanol and i-propanol. These reaction solvents can be used solely or in combination thereof. Alternatively, the reaction can be carried out in neat form without using the reaction solvent.

There is no particular restriction on the amount of the reaction solvent used. It suffices to use 0.01 L or more of the reaction solvent per 1 mol of the optically active tertiary amine of the formula [3]. The reaction solvent is generally preferably used in an amount of 0.03 to 20 L, more preferably 0.05 to 10 L, per 1 mol of the optically active tertiary amine of the formula [3].

There is no particular restriction on the temperature condition. It suffices to carry out the reaction in a temperature range of 20 to 200° C. The reaction temperature is generally preferably in the range of 30 to 175° C., more preferably 40 to 150° C.

There is no particular restriction on the reaction time. It is preferable to carry out the reaction within 48 hours. As the reaction time varies depending on the reaction substrate and the reaction conditions, it is more preferable to monitor the progress of the reaction by analytical means such as gas chromatography, thin-layer chromatography, liquid chromatography or nuclear magnetic resonance spectroscopy and finish the reaction at the time almost all of the reactant materials disappear.

The target optically active 1-(fluoro-, trifluoromethyl- or trifluoromethoxy-substituted phenyl)alkylamine N-monoalkyl derivative of the formula [4] can be obtained by performing ordinary post-treatment on the reaction solution. In the case of the inorganic or organic acid being added as the additive, the target optically active 1-(fluoro-, trifluoromethyl- or trifluoromethoxy-substituted phenyl)alkylamine N-monoalkyl derivative of the formula [4] can be efficiently recovered in free base form by filtering out the transition metal catalyst from the reaction solution, condensing the filtrate, neutralizing the condensed filtrate with an aqueous solution of inorganic base e.g. sodium hydroxide, potassium hydroxide or potassium carbonate, extracting the neutralized solution with an organic solvent e.g. toluene, methylene chloride or ethyl acetate followed by condensing the recovered organic phase.

The optically active 1-(fluoro-, trifluoromethyl- or trifluoromethoxy-substituted phenyl)alkylamine N-monoalkyl derivative of the formula [4] can be purified to a high-purity product by converting the N-monoalkyl derivative to the inorganic or organic acid salt and subjecting the inorganic or organic acid salt to recrystallization. The optically active secondary amine of the formula [1] or the optically active tertiary amine of the formula [3] may also be purified in the same way i.e. by converting the amine to an inorganic or organic acid salt and subjecting the salt to recrystallization. (The former example is discussed in International Publication WO 2004/022521.) In order to maximize the high-productivity merit of conducting the asymmetric reduction and reductive alkylation steps in one-pot reaction process as one feature of the present invention, however, it is not always preferable to subject the salt of the optically active secondary amine of the formula [1] to recrystallization purification. In the case of subjecting the salt of the optically active tertiary amine of the formula [3] to recrystallization purification, the suitable form of the salt for efficient improvements in both of chemical purity and diastereomeric excess has not been yet found. For production of the optically active 1-(fluoro-, trifluoromethyl- or trifluoromethoxy-substituted phenyl)alkylamine N-monoalkyl derivative of the formula [4], it is thus most effective to, after forming the final target compound at the hydrogenolysis step, convert the final target compound to the inorganic or organic acid salt and subject the salt to recrystallization purification.

There is no particular restriction on the enantiomeric excess of the optically active 1-(fluoro-, trifluoromethyl- or trifluoromethoxy-substituted phenyl)alkylamine N-monoalkyl derivative of the formula [4] to be converted to the salt form. It suffices that the optically active 1-(fluoro-, trifluoromethyl- or trifluoromethoxy-substituted phenyl) alkylamine N-monoalkyl derivative of the formula [4] has an enantiomeric excess of 50% ee or higher.

Examples of the inorganic acid usable for conversion of the N-monoalkyl derivative to the salt form are carbonic acid, hydrochloric acid, sulfuric acid, nitric acid, hydrobromic acid, hydriodic acid, phosphoric acid, boric acid and perchloric acid. Among others, hydrochloric acid, sulfuric acid and hydrobromic acid are preferred. Particularly preferred are hydrochloric acid and hydrobromic acid.

Examples of the organic acid usable for conversion of the N-monoalkyl derivative to the salt form are aliphatic carboxylic acids such as acetic acid, propionic acid, butyric acid, isobutyric acid, valeric acid, isovaleric acid, hexanoic acid, heptanoic acid, cyclohexane carboxylic acid, octanoic acid, phenylacetic acid and 3-phenylpropionic acid, haloalkyl carboxylic acids such as chloroacetic acid, dichloroacetic acid, trichloroacetic acid, fluoroacetic acid, difluoroacetic acid, trifluoroacetic acid, bromoacetic acid, iodoacetic acid, 2-chloropropionic acid and 3-chloropropionic acid, unsaturated carboxylic acids such as acrylic acid, crotonic acid, citraconic acid, maleic acid, fumaric acid and cis- or trans-cinnamic acid, aromatic carboxylic acids such as benzoic acid, o-, m- or p-toluylic acid, o-, m- or p-fluorobenzoic acid, o-, m- or p-chlorobenzoic acid, o-, m- or p-bromobenzoic acid, o-, m- or p-iodobenzoic acid, o-, m- or p-hydroxybenzoic acid, o-, m- or p-anisic acid, o-, m- or p-aminobenzoic acid, o-, m- or p-nitrobenzoic acid, o-, m- or p-cyanobenzoid acid, benzene-o-, m- or p-dicarboxylic acid (phthalic acid, isophthalic acid, terephthalic acid), α, β- or γ-picolinic acid, 2,6-pyridinedicarboxylic acid and 1- or 2-naphthoic acid, sulfonic acids such as methanesulfonic acid, chloromethanesulfonic acid, trifluoromethanesulfonic acid, benzenesulfonic acid, p-toluenesulfonic acid and p-phenolsulfonic acid, optically active carboxylic acids such as lactic acid, malic acid, tartaric acid, dibenzoyltartaric acid, 2-phenylpropionic acid, mandelic acid, camphoric acid and cis-2-benzamidocyclohexane carboxylic acid, optically active sulfonic acids such as phenylethane sulfonic acid and 10-camphorsulfonic acid, optically active phosphoric acids such as 2,2'-(1,1'-binaphthyl)phosphoric acid, optically active amino acids such as 4-aminobutyric acid, phenylglycine and aspartic acid, optically active N-acylamino acids such as pyroglutamic acid, N-acetyl-3,5-dibromo-tyrosine, N-acyl-phenylalanine, N-acyl-aspartic acid, N-acyl-glutamic acid and N-acyl-proline (where the N-acyl moiety is acetyl, benzyloxycarbonyl, benzoyl, benzenesulfonyl, p-toluenesulfonyl and the like) and other organic acids such as formic acid, oxalic acid, malonic acid, succinic acid, adipic acid, pimelic acid, cyanoacetic acid, citric acid, glycolic acid, glyoxalic acid, pyruvic acid, levulinic acid, oxaloacetic acid, mercaptoacetic acid, phenoxyacetic acid and picric acid. (Each of the optically active carboxylic acids, the optically active sulfonic acids, the optically active phosphoric acids, the optically active amino acids and the optically active N-acylamino acids contains optical isomers, both of which are usable for conversion of the N-monoalkyl derivative to the salt form. Among others, fumaric acid, phthalic acid, benzenesulfonyl acid, p-toluenesulfonyl acid, malic acid, tartaric acid and mandelic acid are preferred. More preferred is p-toluenesulfonyl acid. The recrystallization purification of the salt of the optically active 1-(trifluoromethyl-substituted phenyl)alkylamine N-monoalkyl derivative of the formula [11] enables efficient improvements in both of chemical purity and enantiomeric excess.

There is no particular restriction on the amount of the inorganic or organic acid used for conversion of the N-monoalkyl derivative to the salt form. It suffices to use 1 mol or more of the inorganic or organic acid per 1 mol of the optically active 1-(fluoro-, trifluoromethyl- or trifluoromethoxy-substituted phenyl)alkylamine N-monoalkyl derivative of the formula [4]. The inorganic or organic acid is generally preferably used in the amount of 1 to 5 mol, more preferably 1 to 3 mol, per 1 mol of the optically active 1-(fluoro-, trifluoromethyl- or trifluoromethoxy-substituted phenyl)alkylamine N-monoalkyl derivative of the formula [4].

The technique of conversion of the optically active 1-(fluoro-, trifluoromethyl- or trifluoromethoxy-substituted phenyl)alkylamine N-monoalkyl derivative of the formula [4] to the salt form can be selected appropriately depending on the combination of the N-monoalkyl derivative and the inorganic or organic acid. In general, the optically active 1-(fluoro-, trifluoromethyl- or trifluoromethoxy-substituted phenyl)alkylamine N-monoalkyl derivative of the formula [4] can be converted to the salt form by directly mixing the N-monoalkyl derivative and the inorganic or organic acid into the recrystallization solvent, or by preparing the respective solutions of the N-monoalkyl derivative and of the inorganic or organic acid in advance and mixing the solutions together. In the case of using the inorganic or organic acid as the additive in the hydrogenolysis step, it is industrially desirable to select the additive acid as appropriate so that the additive acid can also be used as the inorganic or organic acid for conversion of the N-monoalkyl derivative to the salt form. More specifically, the reaction solution can be directly subjected to salt recrystallization purification upon filtering out the palladium catalyst from the reaction solution after the hydrogenolysis.

There is no particular restriction on the recrystallization solvent used for recrystallization purification of the salt as long as the recrystallization solvent does not react with the optically active 1-(fluoro-, trifluoromethyl- or trifluoromethoxy-substituted phenyl)alkylamine N-monoalkyl derivative of the formula [4], the inorganic or organic acid and salts derived therefrom. The recrystallization solvent can be selected appropriately depending on the enantiomeric excess of the salt before the purification or the target enantiomeric excess and recovery rate of the salt after the purification.

Examples of the recrystallization solvent usable for recrystallization purification of the salt are aliphatic hydrocarbon solvents such as n-pentane, n-hexane, cyclohexane and n-heptane, aromatic hydrocarbon solvents such as benzene, toluene, ethyl benzene, xylene and mesitylene, halogenated hydrocarbon solvents such as methylene chloride, chloroform and 1,2-dichloroethane, ether solvents such as diethyl ether, tetrahydrofuran, t-butyl methyl ether and 1,4-dioxane, ketone solvents such as acetone, methyl ethyl ketone and methyl i-butyl ketone, ester solvents such as ethyl acetate and n-butyl acetate, nitrile solvents such as acetonitrile and propionitrile, alcohol solvents such as methanol, ethanol, n-propanol, i-propanol and n-butanol and water. Among others, n-hexane, n-heptane, toluene, methylene chloride, t-butyl methyl ether, acetone, ethyl acetate, acetonitrile, methanol, ethanol, n-propanol and i-propanol are preferred. More preferred are n-heptane, toluene, methanol, ethanol and i-propanol. These recrystallization solvents can be used solely or in combination thereof.

There is no particular restriction on the amount of the recrystallization solvent used for recrystallization purification of the salt as long as all or some of the yet-to-be-purified salt can be solved in the recrystallization solvent under heating. The amount of the recrystallization solvent can be adjusted appropriately depending on the enantiomeric excess of the salt before the purification or the target enantiomeric excess and recovery rate of the salt after the purification. More specifically, it suffices to use 0.01 L or more of the recrystallization solvent per 1 mol of the salt of the optically active 1-(fluoro-, trifluoromethyl- or trifluoromethoxy-substituted phenyl)alkylamine N-monoalkyl derivative. The recrystallization solvent is generally preferably used in the amount of 0.03 to 20 L, more preferably 0.05 to 10 L, per 1 mol of the salt of the optically active 1-(fluoro-, trifluoromethyl- or trifluoromethoxy-substituted phenyl)alkylamine N-monoalkyl derivative.

In the salt recrystallization purification, the crystalline salt may be precipitated out smoothly and efficiently by the addition of a seed crystal. (When the appropriate precipitation conditions are adopted, the seed crystal is not necessarily added.)

There is no particular restriction on the amount of the seed crystal used. It suffices to use 0.00001 mol or more of the seed crystal per 1 mol of the salt before the purification. The seed crystal is generally preferably used in the amount of 0.0001 to 0.1 mol, more preferably 0.0002 to 0.05 mol, per 1 mol of the salt before the purification.

There is no particular restriction on the temperature condition of the salt recrystallization purification. The recrystallization purification temperature can be selected as appropriate depending on the boiling and freezing points of the recrystallization solvent used. It is generally preferable to dissolve the salt into the recrystallization solvent at around a temperature from room temperature (25° C.) to the boiling point of the recrystallization solvent and then precipitate out the crystal at a temperature from −40 to +80° C.

As the recrystallization purification can improve the enantiomeric excess of the precipitated crystalline salt, it is possible to obtain the salt of the optically active 1-(fluoro-, trifluoromethyl- or trifluoromethoxy-substituted phenyl)alkylamine N-monoalkyl derivative of the formula [4] with high enantiomeric excess by recovering the crystallized precipitated salt by filtration etc. The recrystallization purification may be conducted repeatedly in order to provide the salt with higher enantiomeric excess. The obtained salt can be recovered in free base form by neutralizing the salt with an aqueous solution of inorganic base e.g. sodium hydroxide, potassium hydroxide or potassium carbonate, extracting the neutralized solution with an organic solvent e.g. toluene, methylene chloride or ethyl acetate followed by condensing the recovered organic phase. The recovered free base may be purified to a higher purity through purification process such as activated carbon treatment, distillation or recrystallization as required. The obtained salt can also be used by itself as important intermediates for medicines and agricultural chemicals.

Specific examples of the optically active 1-(fluoro-, trifluoromethyl- or trifluoromethoxy-substituted phenyl)alkylamine N-monoalkyl derivative of the formula [4] produced according to the present invention are (R)-1-(2-fluorophenyl)ethylamine N-monomethyl, (S)-1-(2-fluorophenyl)ethylamine N-monomethyl, (R)-1-(3-fluorophenyl)ethylamine N-monomethyl, (S)-1-(3-fluorophenyl)ethylamine N-monomethyl, (R)-1-(4-fluorophenyl)ethylamine N-monomethyl, (S)-1-(4-fluorophenyl)ethylamine N-monomethyl, (R)-1-(3,5-difluorophenyl)ethylamine N-monomethyl, (S)-1-(3,5-difluorophenyl)ethylamine N-monomethyl, (R)-1-(2-fluorophenyl)propylamine N-monomethyl, (S)-1-(2-fluorophenyl)propylamine N-monomethyl, (R)-1-(3-fluorophenyl)propylamine N-monomethyl, (S)-1-(3-fluorophenyl)propylamine N-monomethyl, (R)-1-(4-fluorophenyl)propylamine N-monomethyl, (S)-1-(4-fluorophenyl)propylamine N-monomethyl, (R)-1-(3,5-difluorophenyl)propylamine N-monomethyl, (S)-1-(3,5-difluorophenyl)propylamine N-monomethyl, (R)-1-(2-fluorophenyl)ethylamine N-monoethyl, (S)-1-(2-fluorophenyl)ethylamine N-monoethyl, (R)-1-(3-fluorophenyl)ethylamine N-monoethyl, (S)-1-(3-fluorophenyl)ethylamine N-monoethyl, (R)-1-(4-fluorophenyl)ethylamine N-monoethyl, (S)-1-(4-fluorophenyl)ethylamine N-monoethyl, (R)-1-(3,5-difluorophenyl)ethylamine N-monoethyl, (S)-1-(3,5-difluorophenyl)ethylamine N-monoethyl, (R)-1-(2-fluorophenyl)propylamine N-monoethyl, (S)-1-(2-fluorophenyl)propylamine N-monoethyl, (R)-1-(3-fluorophenyl)propylamine N-monoethyl, (S)-1-(3-fluorophenyl)propylamine N-monoethyl, (R)-1-(4-fluorophenyl)propylamine N-monoethyl, (S)-1-(4-fluorophenyl)propylamine N-monoethyl, (R)-1-(3,5-difluorophenyl)propylamine N-monoethyl, (S)-1-(3,5-difluorophenyl)propylamine N-monoethyl, (R)-1-(2-trifluoromethylphenyl)ethylamine N-monomethyl, (S)-1-(2-trifluoromethylphenyl)ethylamine N-monomethyl, (R)-1-(3-trifluoromethylphenyl)ethylamine N-monomethyl, (S)-1-(3-trifluoromethylphenyl)ethylamine N-monomethyl, (R)-1-(4-trifluoromethylphenyl)ethylamine N-monomethyl, (S)-1-(4-trifluoromethylphenyl)ethylamine N-monomethyl, (R)-1-(3,5-bis-trifluoromethylphenyl)ethylamine N-monomethyl, (S)-1-(3,5-bis-trifluoromethylphenyl)ethylamine N-monomethyl, (R)-1-(2-trifluoromethylphenyl)propylamine N-monomethyl, (S)-1-(2-trifluoromethylphenyl)propylamine N-monomethyl, (R)-1-(3-trifluoromethylphenyl)propylamine N-monomethyl, (S)-1-(3-trifluoromethylphenyl)propylamine N-monomethyl, (R)-1-(4-trifluoromethylphenyl)propylamine N-monomethyl, (S)-1-(4-trifluoromethylphenyl)propylamine N-monomethyl, (R)-1-(3,5-bis-trifluoromethylphenyl)propylamine N-monomethyl, (S)-1-(3,5-bis-trifluoromethylphenyl)propylamine N-monomethyl, (R)-1-(2-trifluoromethylphenyl)ethylamine N-monoethyl, (S)-1-(2-trifluoromethylphenyl)ethylamine N-monoethyl, (R)-1-(3-trifluoromethylphenyl)ethylamine N-monoethyl, (S)-1-(3-trifluoromethylphenyl)ethylamine N-monoethyl, (R)-1-(4-trifluoromethylphenyl)ethylamine N-monoethyl, (S)-1-(4-trifluoromethylphenyl)ethylamine N-monoethyl, (R)-1-(3,5-bis-trifluoromethylphenyl)ethylamine N-monoethyl, (S)-1-(3,5-bis-trifluoromethylphenyl)ethylamine N-monoethyl, (R)-1-

(2-trifluoromethylphenyl)propylamine N-monoethyl, (S)-1-(2-trifluoromethylphenyl)propylamine N-monoethyl, (R)-1-(3-trifluoromethylphenyl)propylamine N-monoethyl, (S)-1-(3-trifluoromethylphenyl)propylamine N-monoethyl, (R)-1-(4-trifluoromethylphenyl)propylamine N-monoethyl, (S)-1-(4-trifluoromethylphenyl)propylamine N-monoethyl, (R)-1-(3,5-bis-trifluoromethylphenyl)propylamine N-monoethyl, (S)-1-(3,5-bis-trifluoromethylphenyl)propylamine N-monoethyl, (R)-1-(2-trifluoromethoxyphenyl)ethylamine N-monomethyl, (S)-1-(2-trifluoromethoxyphenyl)ethylamine N-monomethyl, (R)-1-(3-trifluoromethoxyphenyl)ethylamine N-monomethyl, (S)-1-(3-trifluoromethoxyphenyl)ethylamine N-monomethyl, (R)-1-(4-trifluoromethoxyphenyl)ethylamine N-monomethyl, (S)-1-(4-trifluoromethoxyphenyl)ethylamine N-monomethyl, (R)-1-(3,5-bis-trifluoromethoxyphenyl)ethylamine N-monomethyl, (S)-1-(3,5-bis-trifluoromethoxyphenyl)ethylamine N-monomethyl, (R)-1-(2-trifluoromethoxyphenyl)propylamine N-monomethyl, (S)-1-(2-trifluoromethoxyphenyl)propylamine N-monomethyl, (R)-1-(3-trifluoromethoxyphenyl)propylamine N-monomethyl, (S)-1-(3-trifluoromethoxyphenyl)propylamine N-monomethyl, (R)-1-(4-trifluoromethoxyphenyl)propylamine N-monomethyl, (S)-1-(4-trifluoromethoxyphenyl)propylamine N-monomethyl, (R)-1-(3,5-bis-trifluoromethoxyphenyl)propylamine N-monomethyl, (S)-1-(3,5-bis-trifluoromethoxyphenyl)propylamine N-monomethyl, (R)-1-(2-trifluoromethoxyphenyl)ethylamine N-monoethyl, (S)-1-(2-trifluoromethoxyphenyl)ethylamine N-monoethyl, (R)-1-(3-trifluoromethoxyphenyl)ethylamine N-monoethyl, (S)-1-(3-trifluoromethoxyphenyl)ethylamine N-monoethyl, (R)-1-(4-trifluoromethoxyphenyl)ethylamine N-monoethyl, (S)-1-(4-trifluromethoxyphenyl)ethylamine N-monoethyl, (R)-1-(3,5-bis-trifluoromethoxyphenyl)ethylamine N-monoethyl, (S)-1-(3,5-bis-trifluoromethoxyphenyl)ethylamine N-monoethyl, (R)-1-(2-trifluoromethoxyphenyl)propylamine N-monoethyl, (S)-1-(2-trifluoromethoxyphenyl)propylamine N-monoethyl, (R)-1-(3-trifluoromethoxyphenyl)propylamine N-monoethyl, (S)-1-(3-trifluoromethoxyphenyl)propylamine N-monoethyl, (R)-1-(4-trifluoromethoxyphenyl)propylamine N-monoethyl, (S)-1-(4-trifluoromethoxyphenyl)propylamine N-monoethyl, (R)-1-(3,5-bis-trifluoromethoxyphenyl)propylamine N-monoethyl and (S)-1-(3,5-bis-trifluoromethoxyphenyl)propylamine N-monoethyl. The present invention is not limited to the above compounds.

EXAMPLES

The present invention will be described below in more detail with reference to the following examples. It should be however noted that the following examples are only illustrative and not intended to limit the invention thereto.

Example 1

Production of Optically Active (R)-1-(3,5-bis-trifluoromethylphenyl)ethylamine N-Monomethyl (Dehydration Condensation)
To 300 ml of toluene, 76.85 g (300.03 mmol, 1 eq) of 3,5-bis-trifluoromethylphenyl methyl ketone, 39.99 g (330.00 mmol, 1.10 eq) of (R)-1-phenyl ethyl amine and 1.23 g (9.02 mmol, 0.03 eq) of zinc chloride were added. The resulting mixture was stirred for 17 hours under reflux condition while removing by-product water by means of a Dien-Stark trap. The reaction conversion rate was determined by gas chromatography to be 99.7%. The reaction solution was sequentially washed with 150 ml of IN aqueous sodium hydroxide solution, 180 ml of 0.5N aqueous acetic acid solution and then 100 ml of saturated sodium chloride solution. The recovered organic phase was dried with anhydrous sodium sulfate, filtered, condensed and vacuum-dried, thereby obtaining 121.29 g of a crude product (toluene-containing crystal form) of an optically active imine of the following formula.

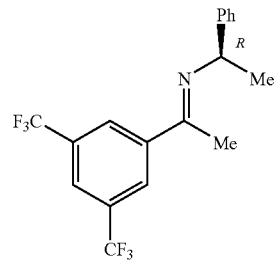

The product yield was quantitative. The gas-chromatographic purity of the crude product was 98.8%. To all of 121.29 g of the crude product, 32 ml of methanol was added. The resulting mixture was washed with stirring for 3 hours at room temperature and for 3 hours under ice cooling, filtered, vacuum-dried, thereby obtaining 98.75 of a high-purity product (crystal form) of the above optically active imine. The total product yield was 91.6%. The gas-chromatographic purity of the high-purity product was 100%. The $^1$H-NMR data of the high-purity product are indicated as follows.

$^1$H-NMR (standard substance: TMS, solvent: CDCl$_3$), δ ppm: 1.55 (d, 6.4 Hz, 3H), 2.33 (s, 3H), 4.87 (q, 6.4 Hz, 1H), 7.24 (Ar—H, 1H), 7.35 (Ar—H, 2H) 7.45 (Ar—H, 2H), 8.31 (Ar—H, 1H), 8.38 (Ar—H, 2H)

(One-Pot Reaction Process of Asymmetric Reduction and Reductive Alkylation)

To 14 ml of methanol, 14.37 g (39.99 mmol, 1 eq) of the high-purity product of the optically active imine obtained by the above dehydration condensation step was added together with 78 mg (0.002 mmol, 0.0005 eq) of 5% platinum/alumina. The resulting mixture was stirred for 16 hours at 25° C. under hydrogen gas pressure of 2 MPa, thereby obtaining a reaction solution of an optically active secondary amine of the following formula.

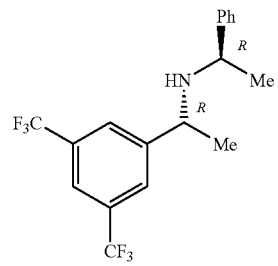

The reaction conversion rate and the diastereomeric were determined by gas chromatography to be 99.9% and 90.1% de, respectively.

To the reaction solution, 6.00 g (199.80 mmol, 5.00 eq) of paraformaldehyde was added under nitrogen gas atmosphere. The resulting mixture was stirred for 47 hours at 100° C.

under hydrogen gas pressure of 2 MPa. The reaction conversion rate was determined by gas chromatography to be 100%. The reaction solution was filtrated. The filtered transition metal catalyst was washed with 15 ml of methanol. The filtrate solution was condensed and vacuum-dried. The residue was diluted with 50 ml of ethyl acetate and washed with 30 ml of water. The recovered organic phase was condensed and vacuum-dried, thereby obtaining 14.85 g of a crude product (oily matter) of optically active tertiary amine of the following formula.

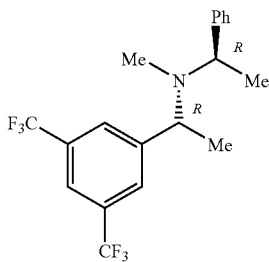

The total one-pot reaction yield was 98.9%. The gas-chromatographic purity and enantiomeric excess of the crude product were 100% and 90.9% de, respectively. The $^1$H-NMR data of the crude product are indicated as follows.

$^1$H-NMR (standard substance: TMS, solvent: CDCl$_3$), δ ppm: 1.37 (d, 6.8 Hz, 3H), 1.38 (d, 6.8 Hz, 3H), 2.00 (s, 3H), 3.76 (q, 6.8 Hz, 1H), 4.00 (q, 6.8 Hz, 1H), 7.20-7.40 (Ar—H, 5H), 7.76 (Ar—H, 1H) 7.82 (Ar—H, 2H)

(Hydrogenolysis)

To 14 ml of methanol, all of 14.85 g (39.56 mmol, 1 eq) of the optically active tertiary amine crude product obtained by the one-pot asymmetric reduction-reductive alkylation reaction, 12.00 g (199.83 mmol, 5.05 eq) of acetic acid and 85 mg (0.02 mmol, 0.0005 eq) of 5% palladium/activated carbon (water content: 50 wt %) were added. The resulting mixture was stirred for 16 hours at 60° C. under hydrogen gas pressure of 0.5 MPa. The reaction conversion rate was determined by gas chromatography to be 100%. The reaction solution was filtered using a filter aid (trade name: Celite), condensed and vacuum-dried. The resulting residue was neutralized (pH>12) with 1000 ml of 3N aqueous sodium hydroxide solution, extracted with 300 ml of ethyl acetate and 300 ml of toluene and washed with 100 ml of saturated sodium chloride solution. The recovered organic phase was dried with anhydrous sodium sulfate, filtered, condensed and vacuum-dried, thereby obtaining 7.55 g of a crude product (oily matter) of optically active (R)-1-(3,5-bis-trifluoromethylphenyl)ethylamine N-monomethyl of the following formula.

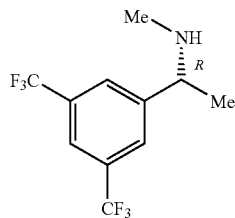

The product yield was 70.4%. The gas-chromatographic purity and enantiomeric excess of the crude product was 97.7% and 90.0% ee, respectively. The $^1$H-NMR data of the crude product are indicated as follows.

$^1$H-NMR (standard substance: TMS, solvent: CDCl$_3$), δ ppm: 1.38 (d, 6.4 Hz, 3H), 1.45 (br, 1H), 2.30 (s, 3H), 3.81 (q, 6.4 Hz, 1H), 7.75 (Ar—H, 1H), 7.80 (Ar—H, 2H)

Example 2

Purification of Optically Active
(R)-1-(3,5-bis-trifluoromethylphenyl)ethylamine
N-monomethyl (Salt Recrystallization Purification)

Into 29.4 ml of i-propanol, 7.36 g (27.13 mmol, 1 eq) of a crude product of optically active (R)-1-(3,5-bis-trifluoromethylphenyl)ethylamine N-monomethyl (gas-chromatographic purity: 99.3%, enantiomeric excess: 89.7% ee) produced in the same manner as in Example 1 and 5.16 g (27.13 mmol, 1.00 eq) of p-toluenesulfonic acid monohydrate were added and dissolved under reflux condition followed by adding thereto 7.4 ml of methanol. The resulting mixture was let standing and cooled to room temperature. The mixture was then stirred for 3 hours so as to precipitate out a crystal. The precipitated crystal was filtered out and vacuum-dried, thereby obtaining 8.76 g of a recrystallization purification product of optically active (R)-1-(3,5-bis-trifluoromethylphenyl)ethylamine N-methyl salt of the following formula.

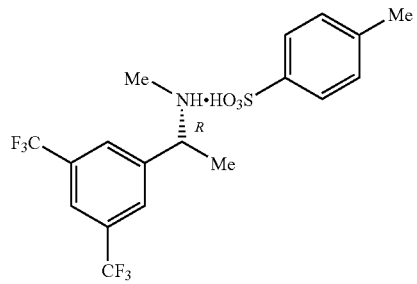

The recovery was 72.8%. The gas-chromatographic purity and enantiomeric excess of the recrystallization purification product were 100% and 97.7% ee, respectively. The recovery was 76.4% on the basis of the optically active isomer (R-isomer).

The recrystallization purification product of the salt was neutralized with 1N aqueous sodium hydroxide solution, extracted with toluene, condensed and vacuum-dried, thereby quantitatively obtaining a high-purity product (free base, oily matter) of optically active (R)-1-(3,5-bis-trifluoromethylphenyl)ethylamine N-monomethyl of the following formula.

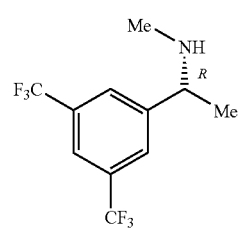

There were no decreases in the gas-chromatographic purity and the enantiomeric excess of the high-purity product.

The invention claimed is:

1. A method for producing an optically active 1-(fluoro-, trifluoromethyl- or trifluoromethoxy-substituted phenyl) alkylamine N-monoalkyl compound of the formula [4], comprising:
   conducting reductive alkylation of an optically active secondary amine of the formula [1] and a formaldehyde (including an equivalent thereof) or lower aldehyde of the formula [2] in the presence of a transition metal catalyst under a hydrogen gas atmosphere, thereby converting the secondary amine to an optically active tertiary amine of the formula [3]; and
   subjecting the tertiary amine to hydrogenolysis

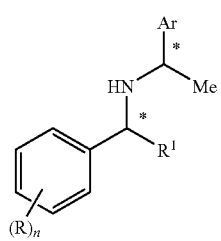

[1]

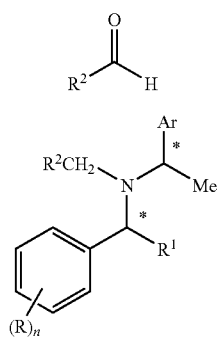

[2]

[3]

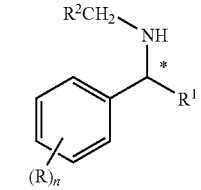

[4]

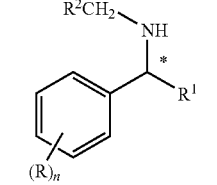

where R represents a fluorine atom, a trifluoromethyl group or a trifluoromethoxy group; n is an integer of 1 to 5; the substitution position is arbitrary; $R^1$ represents an alkyl group having a carbon number of 1 to 6; $R^2$ represents a hydrogen atom or an alkyl group having a carbon number of 1 to 5; Me represents a methyl group; Ar represents a phenyl group or 1- or 2-naphthyl group; and * represents an asymmetric carbon.

2. The method for producing the optically active 1-(fluoro-, trifluoromethyl- or trifluoromethoxy-substituted phenyl) alkylamine N-monoalkyl compound according to claim 1, wherein the optically active secondary amine of the formula [1] is formed by:
   conducting dehydration condensation of a fluoro-, trifluoromethyl- or trifluoromethoxy-substituted phenyl alkyl ketone of the formula [5] and an optically active primary amine of the formula [6], thereby converting the ketone to an optically active imine of the formula [7]; and
   conducting asymmetric reduction of the imine in the presence of a transition metal catalyst under a hydrogen gas atmosphere

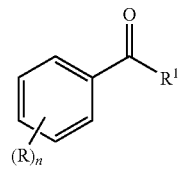

[5]

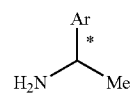

[6]

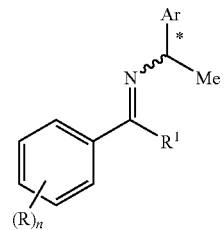

[7]

where R represents a fluorine atom, a trifluoromethyl group or a trifluoromethoxy group; n is an integer of 1 to 5; the substitution position is arbitrary; $R^1$ represents an alkyl group having a carbon number of 1 to 6; Me represents a methyl group; Ar represents a phenyl group or 1- or 2-naphthyl group; the wavy line represents E configuration or Z configuration; and * represents an asymmetric carbon.

3. The method for producing the optically active 1-(fluoro-, trifluoromethyl- or trifluoromethoxy-substituted phenyl) alkylamine N-monoalkyl compound according to claim 2, wherein the optically active tertiary amine of the formula [3] is formed by:
   conducting said asymmetric reduction of the optically active imine of the formula [7] in the presence of the transition metal catalyst under the hydrogen gas atmosphere to provide a reaction solution containing the optically active secondary amine of the formula [1];
   directly adding the formaldehyde (including its equivalent) or lower aldehyde of the formula [2] to the reaction solution; and
   conducting said reductive alkylation of the secondary amine and the formaldehyde or lower aldehyde under the hydrogen gas atmosphere by the reuse of the transition metal catalyst remaining in the reaction solution.

4. The method for producing the optically active 1-(fluoro-, trifluoromethyl- or trifluoromethoxy-substituted phenyl) alkylamine N-monoalkyl compound according to claim 1, wherein the optically active 1-(fluoro-, trifluoromethyl- or trifluoromethoxy-substituted phenyl)alkylamine N-monoalkyl compound of the formula [4] is produced with high purity by converting the N-monoalkyl compound to an inorganic or organic acid salt and subjecting the salt to recrystallization purification.

5. A method for producing an optically active 1-(trifluoromethyl-substituted phenyl)alkylamine N-monoalkyl compound of the formula [11], comprising:
   conducting reductive alkylation of an optically active secondary amine of the formula [8] and a paraformaldehyde of the formula [9] in the presence of a transition metal catalyst under a hydrogen gas atmosphere, thereby converting the secondary amine to an optically active tertiary amine of the formula [10]; and
   subjecting the tertiary amine to hydrogenolysis

[8]

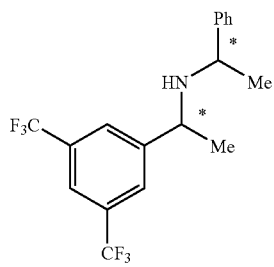

HO(CH₂O)ₘH [9]

[10]

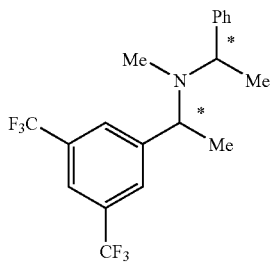

[11]

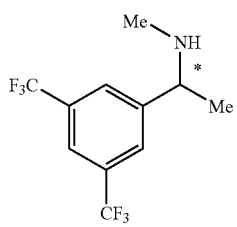

where Me represents a methyl group; Ph represents a phenyl group; m represents a positive integer; and * represents an asymmetric carbon.

6. The method for producing an optically active 1-(trifluoromethyl-substituted phenyl)alkylamine N-monoalkyl compound according to claim 5, wherein the optically active secondary amine of the formula [8] is formed by:

conducting dehydration condensation of a trifluoromethyl-substituted phenyl alkyl ketone of the formula [12] and an optically active primary amine of the formula [13], thereby converting the ketone to an optically active imine of the formula [14]; and conducting asymmetric reduction of the imine in the presence of a transition metal catalyst under a hydrogen gas atmosphere

[12]

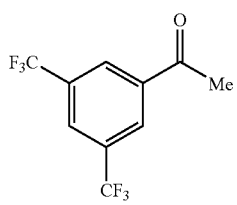

[13]

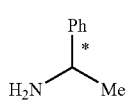

[14]

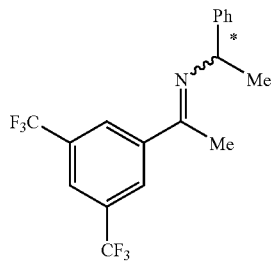

where Me represents a methyl group; Ph represents a phenyl group; the wavy line represents E configuration or Z configuration; and * represents an asymmetric carbon.

7. The method for producing an optically active 1-(trifluoromethyl-substituted phenyl)alkylamine N-monoalkyl compound according to claim 6, wherein the optically active tertiary amine of the formula [10] is formed by:

conducting said asymmetric reduction of the optically active imine of the formula [14] in the presence of the transition metal catalyst under the hydrogen gas atmosphere to provide a reaction solution containing the optically active secondary amine of the formula [8];

directly adding the paraformaldehyde of the formula [9] to the reaction solution; and conducting said reductive alkylation of the secondary amine and the paraformaldehyde under the hydrogen gas atmosphere by the reuse of the transition metal catalyst remaining in the reaction solution.

8. The method for producing an optically active 1-(trifluoromethyl-substituted phenyl)alkylamine N-monoalkyl compound according to claim 5, wherein the optically active 1-(trifluoromethyl-substituted phenyl)alkylamine N-monoalkyl compound of the formula [11] is produced with high purity by converting the N-monoalkyl compound to an inorganic or organic acid salt and subjecting the salt to recrystallization purification.

9. The method for producing the optically active 1-(fluoro-, trifluoromethyl- or trifluoromethoxy-substituted phenyl)alkylamine N-monoalkyl compound according to claim 3, wherein the optically active 1-(fluoro-, trifluoromethyl- or trifluoromethoxy-substituted phenyl)alkylamine N-monoalkyl compound of the formula [4] is produced with high purity by converting the N-monoalkyl compound to an inorganic or organic acid salt and subjecting the salt to recrystallization purification.

10. The method for producing the optically active 1-(fluoro-, trifluoromethyl- or trifluoromethoxy-substituted phenyl)alkylamine N-monoalkyl compound according to claim 3, wherein the optically active 1-(fluoro-, trifluoromethyl- or trifluoromethoxy-substituted phenyl)alkylamine N-monoalkyl compound of the formula [4] is produced with high purity by converting the N-monoalkyl compound to an inorganic or organic acid salt and subjecting the salt to recrystallization purification.

11. The method for producing an optically active 1-(trifluoromethyl-substituted phenyl)alkylamine N-monoalkyl compound according to claim 6, wherein the optically active 1-(trifluoromethyl-substituted phenyl)alkylamine N-monoalkyl compound of the formula [11] is produced with high purity by converting the N-monoalkyl compound to an inorganic or organic acid salt and subjecting the salt to recrystallization purification.

12. The method for producing an optically active 1-(trifluoromethyl-substituted phenyl)alkylamine N-monoalkyl compound according to claim 8, wherein the optically active 1-(trifluoromethyl-substituted phenyl)alkylamine N-monoalkyl compound of the formula [11] is produced with high purity by converting the N-monoalkyl compound to an inorganic or organic acid salt and subjecting the salt to recrystallization purification.

* * * * *